US009259524B2

(12) United States Patent
Weibel

(10) Patent No.: US 9,259,524 B2
(45) Date of Patent: Feb. 16, 2016

(54) DIALYSIS MACHINE, A MANIFOLD FOR THE DIALYSIS MACHINE AND PROCESS

(75) Inventor: Ludwig Daniel Weibel, Waldstatt (CH)

(73) Assignee: Vifor (International) AG, St. Gallen (CH)

( * ) Notice: Subject to any disclaimer, the term of this patent is extended or adjusted under 35 U.S.C. 154(b) by 1202 days.

(21) Appl. No.: 13/254,284

(22) PCT Filed: Feb. 25, 2010

(86) PCT No.: PCT/EP2010/052420
§ 371 (c)(1),
(2), (4) Date: Nov. 7, 2011

(87) PCT Pub. No.: WO2010/100074
PCT Pub. Date: Sep. 10, 2010

(65) Prior Publication Data
US 2012/0150141 A1 Jun. 14, 2012

(30) Foreign Application Priority Data
Mar. 2, 2009 (WO) ................. PCT/EP2009/052430

(51) Int. Cl.
| | | |
|---|---|---|
| A61M 1/36 | (2006.01) | |
| A61M 1/34 | (2006.01) | |
| A61M 5/14 | (2006.01) | |
| A61M 5/168 | (2006.01) | |
| A61M 39/10 | (2006.01) | |
| A61M 1/14 | (2006.01) | |

(52) U.S. Cl.
CPC ............ *A61M 1/3672* (2013.01); *A61M 1/3431* (2014.02); *A61M 1/3437* (2014.02); *A61M 1/3458* (2014.02); *A61M 5/1408* (2013.01); *A61M 1/14* (2013.01); *A61M 1/3675* (2013.01); *A61M 5/16881* (2013.01); *A61M 39/10* (2013.01)

(58) Field of Classification Search
CPC ....... A61M 1/30; A61M 1/302; A61M 1/308; A61M 1/342; A61M 1/3455; A61M 1/3643; A61M 2039/0205; A61M 2039/2433; A61M 2039/2493; A61M 39/04; A61M 39/20; A61M 5/1452; A61M 1/3672; A61M 1/3431; A61M 1/3437; A61M 1/3458; A61M 5/1408; A61M 1/3675; A61M 5/16881; A61M 39/10; A61M 1/14
See application file for complete search history.

(56) References Cited

U.S. PATENT DOCUMENTS

| | | | |
|---|---|---|---|
| 3,908,653 A | * | 9/1975 | Kettering ..................... 604/6.05 |
| 5,015,226 A | | 5/1991 | Polaschegg |
| 5,431,185 A | | 7/1995 | Shannon et al. |

(Continued)

FOREIGN PATENT DOCUMENTS

EP 443324 8/1991

*Primary Examiner* — Emily Schmidt
*Assistant Examiner* — Lauren M Peng
(74) *Attorney, Agent, or Firm* — Dilworth & Barrese, LLP.

(57) ABSTRACT

The present invention relates to a dialysis machine for the purification of blood, a manifold for the dialysis machine as well as to a process for the regeneration of the dialysis bath. It is an object of the present invention to provide a dialysis machine, a manifold for the dialysis machine as well a process which facilitates the administration of medical preparations during a dialysis procedure. In order to solve the object, a dialysis machine according to the present invention comprises tubes (1, 5, 8) connected with a dialyzer (6), means for delivering pharmaceuticals into the tubes and a pump (11) for the transport of blood through the tubes and the dialyzer. The dialysis machine comprises means for administration (4) of at least one pharmaceutical by a suction effect of the pump or by a pressure effect of the pump or by an excess pressure of a gas or a liquid.

18 Claims, 7 Drawing Sheets

(56) References Cited

U.S. PATENT DOCUMENTS

| | | | |
|---|---|---|---|
| 8,394,046 B2 * | 3/2013 | Nuernberger et al. | 604/5.01 |
| 2006/0173395 A1 * | 8/2006 | Brugger | A61M 1/3621 604/6.09 |
| 2007/0062861 A1 | 3/2007 | Lannoy | |
| 2009/0008306 A1 * | 1/2009 | Cicchello et al. | 210/85 |

\* cited by examiner

DIALYSIS MACHINE, A MANIFOLD FOR THE DIALYSIS MACHINE AND PROCESS

BACKGROUND OF THE INVENTION

The present invention relates to a dialysis machine for the purification of blood, a manifold for the dialysis machine as well as to a process for the regeneration of the dialysis bath.

Dialysis works on the principles of the diffusion of solutes and ultrafiltration of fluid across a semi-permeable membrane. Blood flows by one side of a semi-permeable membrane, and a dialysate or fluid flows by the opposite side. Smaller solutes and fluid pass through the membrane. The blood flows in one direction and the dialysate flows in the opposite. The counter-current flow of the blood and dialysate maximizes the concentration gradient of solutes between the blood and dialysate, which helps to remove more urea and creatinine from the blood. The concentrations of solutes (for example potassium, phosphorus, and urea) are undesirably high in the blood, but low or absent in the dialysis solution and constant replacement of the dialysate ensures that the concentration of undesired solutes is kept low on this side of the membrane. The dialysis solution has levels of minerals like potassium and calcium that are similar to their natural concentration in healthy blood. For another solute, bicarbonate, dialysis solution level is set at a slightly higher level than in normal blood, to encourage diffusion of bicarbonate into the blood, to act as a pH buffer to neutralise the metabolic acidosis that is often present in these patients. The levels of the components of dialysate are typically prescribed by a nephrologist according to the needs of the individual patient.

A dialysis machine is known from US 2006/0173395, U.S. Pat. Nos. 4,213,859 A and 4,137,168A.

Document US 2006/0173395 A1 discloses a combined arterial and venous blood tubing set for transport of blood between a patient and a blood processing unit. The set comprises an arterial set component comprising arterial tubing having an arterial patient connector at one end and an arterial unit connector at the other. A venous set component has venous tubing with a venous patient connector at one end and a venous unit connector at the other end. The arterial and venous patient connectors, and the arterial and venous unit connectors, are respectively, substantially, and releasably directly connected to each other. As a result of this, the arterial, and venous set components cooperate to form a loop.

An apparatus for the infusion of medicaments and drugs, in particular heparin, into the partial vacuum region of an extracorporeal blood circuit is described in U.S. Pat. No. 5,015,226 which replaces a heparin pump and which comprises a supply container in the form of a syringe, a shutoff member, which may be a clamp, disposed in the feed conduit, a means for measuring the reduced pressure or partial vacuum in the extracorporeal circuit and a control means. Said control means is connected to the pressure measuring means and the shutoff member and constructed for periodic opening and closing of the shutoff member in dependence upon the measured partial vacuum and the desired amount of medicament. The apparatus may be used in the extracorporeal blood circuit of a dialysis apparatus.

A fluid manifold which includes a housing having a first inlet and an outlet and a plurality of inlets intermediate the first inlet and the outlet is known from U.S. Pat. No. 5,431,185. Document EP 0 443 324 A1 discloses a system for preparation of a fluid intended for medical use.

A dialysis machine is a machine that filters a patient's blood to remove excess water and waste products when the kidneys are damaged, dysfunctional, or missing. Blood is drawn through a specially created vein in the forearm, which is called an arterio-venous (AV) fistula. From the AV fistula, blood is taken to the dialysis machine through flexible tube. The dialysis machine itself can be thought of as an artificial kidney. Inside, it consists of more flexible tube that carries the removed blood to the dialyzer, a bundle of hollow fibers that forms a semipermeable membrane for filtering out impurities. In the dialyzer, blood is diffused with a saline solution called dialysate, and the dialysate is in turn diffused with blood. Once the filtration process is complete, the cleansed blood is returned to the corresponding vein of the patient. Most patients using dialysis due to kidney impairment or failure use a dialysis machine at a special dialysis clinic. Most sessions take about four hours, and typically patients visit the clinic three times per week.

In order to prevent clotting in the course of a dialysis procedure, it is necessary to deliver continuously a pharmaceutical like Heparin into one of the tubes and thus into the blood circulation. Towards the end of a dialysis procedure, it is necessary or at least helpful to administer medicaments like iron sucrose for example Venofer®, erythropoietin (EPO) and the active form of vitamin D in addition to heparin. At the end of a dialysis session, it is helpful to deliver a medicament in order to wash the outlet of the fistula. At least some of the medicaments cannot be administered within a short period. Instead of that, it is necessary to input such a medicament stepwise or continuously into a tube of the dialysis machine during a period of several minutes like ten minutes.

For the delivery of pharmaceuticals during a dialysis procedure, the tube of a dialysis machine comprises one or more injection sites as known from U.S. Pat. No. 6,090,066. An injection site may be an elastic, needle-pierceable membrane and/or a female luer lock connector for connecting an administration device like a syringe or an adapter for a vial with the injection site.

A staff member of a clinic has to take care of several patients at the same time. At the beginning, a staff member has to connect every patient to a dialysis machine. After a few hours at the end of these procedures, the staff member has to input the medicaments to the corresponding tubes of the dialysis machines. Due to the time pressure, it is difficult to administer all medicaments to all patients every day without making any mistake.

SUMMARY OF THE INVENTION

It is therefore an object of the present invention to provide a dialysis machine, a manifold for the dialysis machine as well as a process which facilitates the administration of medical preparations during a dialysis procedure.

In order to solve the object of the invention, a dialysis machine comprises tubes connected with a dialyzer, means for delivering pharmaceuticals into the tubes and a blood pump for the transport of blood through the tubes and the dialyzer. Additionally, the dialysis machine comprises means for delivering at least one pharmaceutical by a suction effect of the pump or by a pressure effect of the pump or by an excess pressure of a gas or a liquid.

Since the delivery of at least one pharmaceutical takes place due to a flow generated by the pump or by an excess pressure within a container, the delivery takes place automatically. Additionally, no further pump or motor is necessary in order to administer the pharmaceutical automatically and thus in an easy manner.

In an embodiment of the invention, a cross section of an inlet path into a tube for the at least one pharmaceutical is small so that it will take at least five minutes, preferably at least ten minutes in order to administer the total volume of the at least one pharmaceutical. A manifold of the dialysis machine may comprise the inlet for the pharmaceutical. Typical pharmaceuticals are an iron preparation like Venofer®, EPO, the active form of vitamin D, a medicament for washing a fistula and/or a medicament like Heparin in order to prevent clotting. This embodiment is especially useful for a pharmaceutical like Venofer® of the Swiss company Vifor (International) AG when it is not allowed to administer the total volume of the at least one pharmaceutical in a quick manner within a short period, for example within one minute. In this embodiment of the invention, it is not necessary to administer a pharmaceutical like Venofer® stepwise by hand or by a motor driven piston and the like. In this embodiment, it is also possible to administer a pharmaceutical like Heparin continuously without the need of a motor driven piston. In this case, an inlet pass into a tube may comprise such a small cross section that the delivery of the total Heparin volume requires a few hours.

In order to control the flow rate of the at least one pharmaceutical, the inlet for the pharmaceutical into a tube may comprise a flexible tube. It is then possible to squeeze the flexible tube in order to reduce the cross section of the flow path.

For example at the end of a dialysis procedure, a staff member has only to start or to activate the delivery of the at least one pharmaceutical. It is for example possible to connect all containers or syringes containing the above mentioned pharmaceuticals with the dialysis machine at the same time, preferably at the beginning of a dialysis procedure. The activation of the delivery of one pharmaceutical may take place by opening of a corresponding valve.

It is no longer necessary to administer the pharmaceutical by hand, by an additional motor or an additional pump. If all containers or syringes containing the pharmaceuticals are connected with the dialysis machine at the beginning of the procedure, a staff member can control this situation during the whole dialysis procedure. This helps not to forget a pharmaceutical or not to apply a pharmaceutical twice. For these reasons, the present invention safes costs and facilitates the administration of at least one pharmaceutical.

If all containers or syringes containing pharmaceuticals for carrying out a dialysis are connected with the dialysis machine at the beginning of the procedure, it is possible to control the activation of the delivery automatically by a control device. This embodiment facilitates additionally the handling of a dialysis machine.

In an embodiment of the invention, the dialysis machine comprises at least one membrane valve in order to control the delivery of a pharmaceutical. A membrane valve is very hygienic and leakproof. It is easy to open or to close a membrane valve automatically.

A membrane valve comprises a housing having a membrane stretched thereacross. The membrane is deflectable towards a flow opening which has an intermediate separating ridge or seat. When the membrane is deflected against the separating ridge respectively the seat, flow communication through the flow opening is interrupted. This deflection can be effected either upon application of a pressure medium to the other side of the membrane, or manually, by moving a bolt against the other side of the membrane. Movement of the bolt is obtained, for example, by a motor driven spindle threaded into the housing or more preferably by magnetic forces. Preferably, the spindle or the bolt are made of transparent material so that the position of the membrane can be visually inspected by checking the position of the bolt within the spindle. The fluid in the housing cannot contact movable parts of the valve.

For this reason, the valve is very hygienic. Additionally, the membrane allows to control the flow rate through the valve, since movement of the membrane in the direction of the seat or separating ridge reduces the cross section of the flow path. Thus, this embodiment of the invention allows to control, especially to increase the delivery period of a pharmaceutical.

In an embodiment of the invention, the dialysis machine or a manifold of the dialysis machine comprises one or more housings for several membrane valves but only one membrane covering the several housings. This embodiment allows a space-saving and costs-saving construction of several membrane valves in order to control the administration of several liquid pharmaceuticals.

In an embodiment of the invention, the at least one pharmaceutical is administered by a suction effect of the blood pump, since the container of the at least one pharmaceutical is connected with a tube on the inlet side of the blood pump and the container is collapsible. In this case, the container shall not contain an additional gas and not comprise a further opening during the administration of the pharmaceutical. The blood pump generates a suction force within the tube on the inlet site. Due to this suction force, the liquid content of the collapsible container will flow into the tube for example after opening of a corresponding valve. Since there is no further fluid connection between the container and the environment in the course of the administration, the administration will stop automatically. A gas cannot arrive at the tube, since the pharmaceutical container only contains the liquid pharmaceutical.

If the container is not flexible respectively collapsible, it may be sufficient that the container contains the liquid pharmaceutical as well as a defined gas volume. Further, the container shall not comprise a further opening at least during the administration of the pharmaceutical. In this case, the liquid pharmaceutical must border to the outlet of the container before activating the administration of the liquid pharmaceutical. In order to achieve this result, the outlet of the container is preferably at the bottom, when the container is connected with the tube. In the course of the administration, a depression will occur within the container and will stop the administration in due time. If the container contains sufficient liquid pharmaceutical, a gas like air will not arrive at the tube since the administration of the pharmaceutical stops when the depression force within the container corresponds with said suction force.

Such a container may be provided by connecting a first container containing the pharmaceutical with a second container containing the gas. The first pharmaceutical container is connected with the tube on the inlet side of the pump. This embodiment allows the use of a conventional pharmaceutical container containing the desired pharmaceutical like a syringe or a vial.

If the conventional container is a syringe, the needle of the syringe shall be connected with the tube on the inlet side of the pump for example with a corresponding injection site. A second container containing the gas shall be connected with the opposite side of the syringe. In order to provide the connection between the second gas container and the syringe, the second container may comprise an outlet in the form of a needle penetrating the piston of the syringe.

A conventional container may be an ampoule or a vial with a pierceable rubber stopper as known from WO 2007/082325. There is a well-known conventional adapter for such an ampoule or such a vial comprising a needle with an inlet path and an outlet path. The second container containing the gas shall be connected with the inlet path of the needle. The outlet path of the needle shall be connected with the tube on the inlet side of the pump. The needle of the adapter penetrates the rubber stopper in order to provide said connections.

In such a way, there is a first conventional container, namely a syringe or a vial containing a liquid pharmaceutical connected with the tube on the inlet side of the pump. Additionally, there is a second container comprising the gas and a connection between the first and the second container. The relationship between the liquid volume and the gas volume is adjusted in such manner that the administration of the pharmaceutical stops automatically in due time that means that the desired volume of the pharmaceutical will flow into the tube but not the gas. The administration of the pharmaceutical stops when the depression force within the second container equals or corresponds with said suction force.

In an embodiment of the invention, the connection between said first and said second container comprises a reduction valve in order to control the administration and/or the corresponding flow rate. Additionally or alternatively, the connection between the outlet of the pharmaceutical container and the inlet into a tube of the dialysis machine may comprises a reduction valve in order to control the administration and/or the corresponding flow rate.

A conventional adapter for a conventional ampoule (vial) with a pierceable rubber stopper typically comprises a female luer lock. On the other side, a dialysis machine also comprises an injection sites with a female luer lock typically. For this reason, the dialysis machine may comprise at least one connecting piece making a connection between two female luer lock.

In a further embodiment of the invention, an injection site comprises a male luer lock in order to avoid said connecting piece. Alternatively, the adapter for the vial comprises a male luer lock in order to avoid said connection piece.

If the conventional container is a syringe, it is necessary to avoid a movement of the piston of the syringe during piercing with a needle to connect to the gas container. For this reason a piercing needle may comprise a thread. It is then possible to turn the needle downward into the piston thereby avoiding any displacement of the piston. As an alternative, the needle may comprise a back-action pliers. A piston of a conventional syringe containing a pharmaceutical comprises a clearance. The back-action pliers may grip the inside wall of the clearance in order to fix the piston. It is then possible to penetrate the piston by the needle without moving the piston.

In an embodiment of the invention, means for delivering the at least one pharmaceutical by a pressure effect of the pump comprise a main line and a bypass line for the main line. The main line may replace a section of a tube on the outlet side of the pump or may be a section of said tube. One end of a first section of the bypass line is connected with the main line and the other end of the first section of the bypass line is connected with an inlet into a pharmaceutical container, preferably with an inlet on the top of the container. The second section of the bypass line is a fluid connection between an outlet of the pharmaceutical container, preferably at the bottom of the container and the main line. Said fluid connection respectively second section is discharged downstream into the main line so that blood will flow into the first section of the bypass, afterwards through the container and afterwards through said further fluid connection back into the main line. Due to the bypass line, the pharmaceutical will flow from the container into the main line on the pressure side. Preferably, the container contains only the pharmaceutical but not a gas. In this case, a gas will not flow into the main line. Since all dialysis lines contain a bubble trap respectively air trap before the blood is entering the patient again, gas from the containers that accidentally enters the blood stream will be captured.

As a rule, the cross sections of the first and/or second section of the bypass line determine the flow rate of the pharmaceutical into the main line. If the bypass line comprises a valve, the cross section of the valve may determine or influence the flow rate of the pharmaceutical additionally. The relevant cross sections which determine the flow rate of the pharmaceuticals are preferably designed in such a manner that the administration of the corresponding pharmaceuticals takes place within a desired period. For example, if Venofer® is the pharmaceutical, the relevant cross sections are so designed that the administration will last for at least five minutes, preferably for ten to twenty or up to thirty minutes.

The container may be a conventional container like a syringe or a vial with a rubber stopper for the above mentioned reasons.

In an embodiment of the invention, a manifold comprises said mainline and said bypass line. In an embodiment of the invention, one end of the main line is provided with a dialyzer connector for connecting this end with a female locking adapter respectively female connector of a dialyzer. The other end of the main line is provided with such a female locking adapter for the dialyzer connector. A dialyzer connector is a standardized male locking adapter for connecting a tube of a dialysis machine with the female locking adapter respectively connector of a dialyzer. Since the main line comprises such a standardized connector system for use in a dialyzer, it is possible to connect the manifold with every known dialysis machine comprising the standardized locking system. It is not necessary to redesign the known dialysis machines.

In an embodiment of the invention, the manifold comprises at least two bypass lines wherein every bypass line comprises means for connecting the two sections of a bypass line with an inlet and outlet of a pharmaceutical container as described above. In this case, it is possible to insert several pharmaceutical containers into the manifold at the same time which facilitates the handling for the above mentioned reasons. The first sections of the bypass lines comprise preferably a common inlet line connected with the main line in order to save space and costs. It is possible but not advisable that there is a common outlet line of the second sections of the bypass lines. If there is a common outline line, if is possible that a first pharmaceutical comes into a direct contact with a second pharmaceutical which may cause an undesired chemical reaction. For this reason, it is of advantage that there is no common outlet line in order to exclude an undesired effect.

In an embodiment of the invention, the bypass line or the bypass lines comprise at least one valve for activating the administration of a pharmaceutical. The valve or the valves are preferably membrane valve(s). Due to the valve(s), it is possible to control the administration of the pharmaceuticals by hand or automatically by a control device. Every housing of a valve may be an injection molding part so that the production costs are low. The production costs for the corresponding membrane are also low. For this reason, at least the housing(s) and the membrane or membranes may be disposable parts. Since the bolt or bolts of the membrane valve(s) do not come into contact with the blood, it is possible to reuse the bolt(s) in order to safe costs. For this reason, the manifold comprises in an embodiment of the invention only the housing or the housings of membrane valve(s) which are covered by one or more membranes but not the bolt(s) of the valve(s). In this case, the bolt(s) may be a part or parts of a further device comprising means for controlling and moving the bolts in order to close and/or to open the corresponding valves. For example, the further device comprises magnetic means for moving the bolt(s) or the membrane in a manner as known from U.S. Pat. No. 3,942,759. The further device may comprise a pre-stressed spring for closing a membrane valve and a coil for opening the valve.

The manifold can be composed of or comprise one or two injection molding parts which are made of plastic. In this case, the production costs are low. For this reason, the manifold may be a disposable part which is of advantage for hygienic reasons.

In an embodiment of the invention, the lines of the manifold are transparent in order to check the blood flow through the main line and the bypass line(s).

It is not necessary to connect the manifold directly with the dialyzer. It is also possible to connect both ends of the main line with appropriate ends of the tubes. However, it is then necessary to modify the common design of tubes for a dialyzer machine. In this case, it is not of great advantage that the main line of the manifold is provided with a dialyzer connector and the corresponding locking adapter. Since a modification of the tubes is necessary, the use of other locking means respectively connector systems is possible without any problems.

If a manifold is connected with a tube on the inlet side of the pump, the manifold may comprise one or more containers filled with a gas and means for connecting each gas container with an inlet of a pharmaceutical container. A means for connecting each gas container with an inlet of a pharmaceutical container may be an adapter for a vial or a needle for penetrating the piston of a syringe. Further, the manifold may comprise means in order to connect an outlet of the container containing the pharmaceutical with an injection site of the tube.

In an embodiment of the invention the manifold installed on the inlet side of the pump comprises at least one gas container with a tunable volume. A container comprising a tunable volume is known for example from US-2008-0200886 A1. The gas container may comprise a movable piston in order to adjust a desired volume in dependence of the volume of the pharmaceutical container. In order to avoid a leak, the gas container may comprise a flexible membrane. Means like a piston are able to change the position of the membrane and thus the volume of the gas container. The gas container may comprise one or more latching positions for means like a piston in order to assist the adjustment of a desired volume of the gas container.

It is known from the state of the art that it is of advantage to change the flow rate of Heparin in the course of a dialysis session. The present invention makes it possible to adapt the flow rate of Heparin or a corresponding pharmaceutical to a desired flow rate for example by controlling an appropriate valve. Additionally or alternatively, several pharmaceutical containers containing Heparin are connected with the dialysis machine. The pharmaceutical containers containing Heparin may be inserted into a manifold according to the present invention. It is then possible to increase the Heparin flow rate by opening corresponding valves in order to activate the administration of Heparin of an additional pharmaceutical container.

In an embodiment of the invention, the outlet of a pharmaceutical container is connected with a tube of the dialysis machine. An inlet of the pharmaceutical container is connected with a flexible bag containing an infusion solution. The infusion solution may flow through the pharmaceutical container due to gravitation. In this way, the pharmaceutical will arrive at the tube of the dialysis device.

DESCRIPTION OF THE PREFERRED EMBODIMENTS

Figure 1:
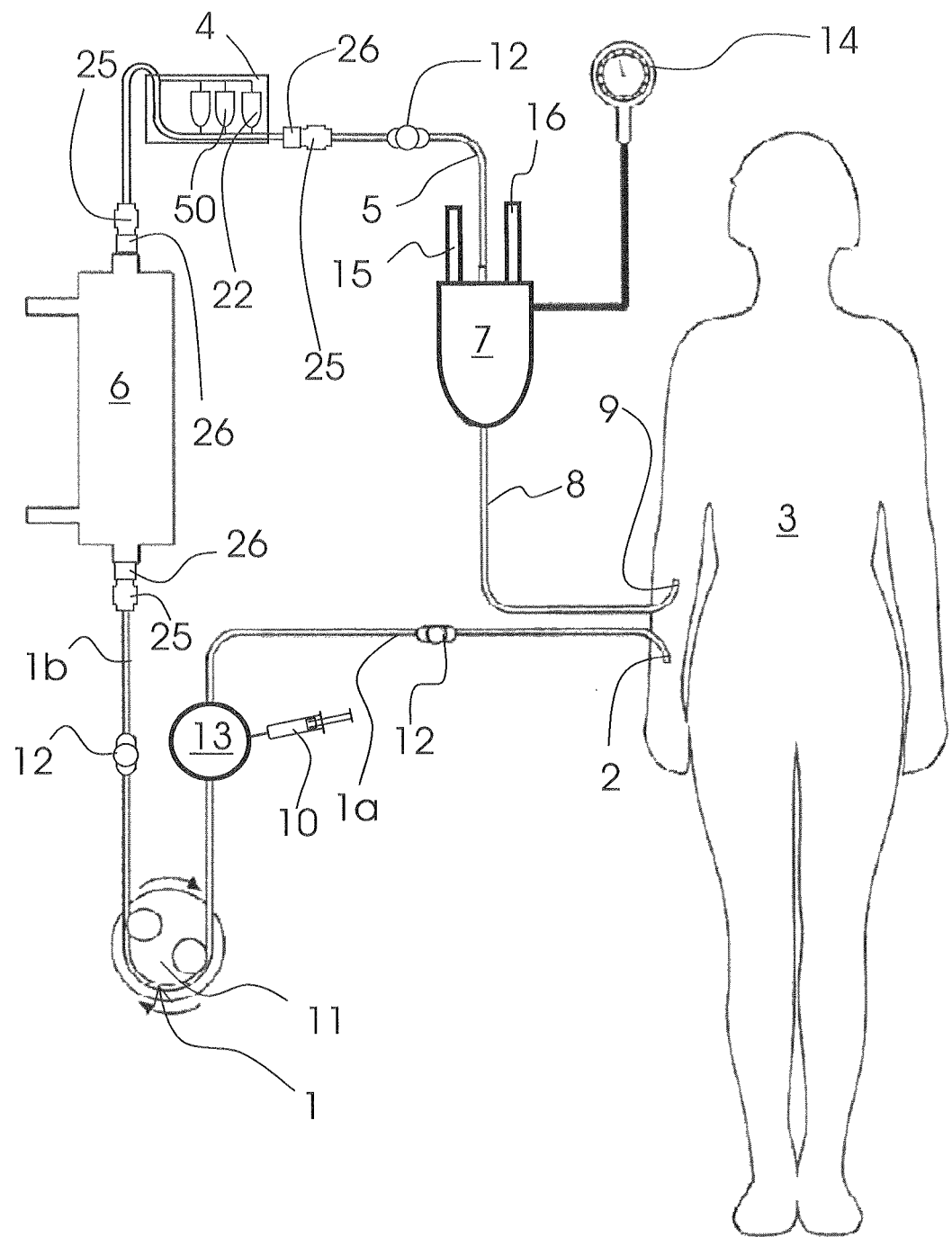
FIG. 1 is a dialysis machine.

The dialysis machine of FIG. 1 comprises a first plastic tube 1 which is connected with the AV fistula 2 of a patient 3 on one side and with an inlet of a dialyzer 6 on the other side. A second plastic tube 5 is connected with an outlet of a manifold 4 on one side and with an inlet on the top of an air trap 7 on the other side. A third plastic tube 8 is connected with an outlet at the bottom of the air trap 7 on one side and with an inlet into the vein 9 of the forearm of the patient 3 on the other side. The inlet of the manifold 4 is connected with an outlet at the top of the dialyzer 6. It is also possible to arrange the manifold between the inlet of the dialyzer and the tube 1. However, in this case, it is not possible to insert a container into the manifold containing a pharmaceutical which is not allowed to pass the dialyzer 6.

A dialysis machine may comprise a snubber 13 arranged between the AV fistula 2 and the peristaltic pump 11. In order to prevent clotting, a Heparin pump 10 may be connected with one of the plastic tubes, preferably with the snubber 13 as known from the state of the art. In order to transport the blood of the patient 3 through the tubes, the air trap and the dialyzer, the dialysis machine comprises a peristaltic pump 11 (blood pump) acting on the first tube 1. As a result, the tube 1 is divided into a suction side 1a and a pressure side 1b. The suction side 1a is between the fistula 2 and the inlet side of the blood pump 11. The pressure side 1b is between the outlet side of the blood pump 11 and the dialyzer 6. The tubes may comprise several injection sites 12 in order to administer medicaments as known from the state of the art. A first injection site may be arranged between the AV fistula 2 and the peristaltic pump 11 (suction side 1a). A second injection site may be arranged between the peristaltic pump 11 and the dialyzer 6 (pressure side 1b). A third injection site may be arranged between the dialyzer 6 and the air trap 7. Typically, an injection site 12 comprises a T-shaped junction with a female luer lock and a diaphragm. The air trap 7 is connected with a pressure gauge 14 for controlling the pressure and thus the air content in the air trap 7. An inlet 15 is connected with the upper end of the air trap 7 in order to feed pure water in the air trap 6. An open port 16 on the top of the air trap 7 can also be used to administer a pharmaceutical or to manually degas the air trap.

Figure 2:
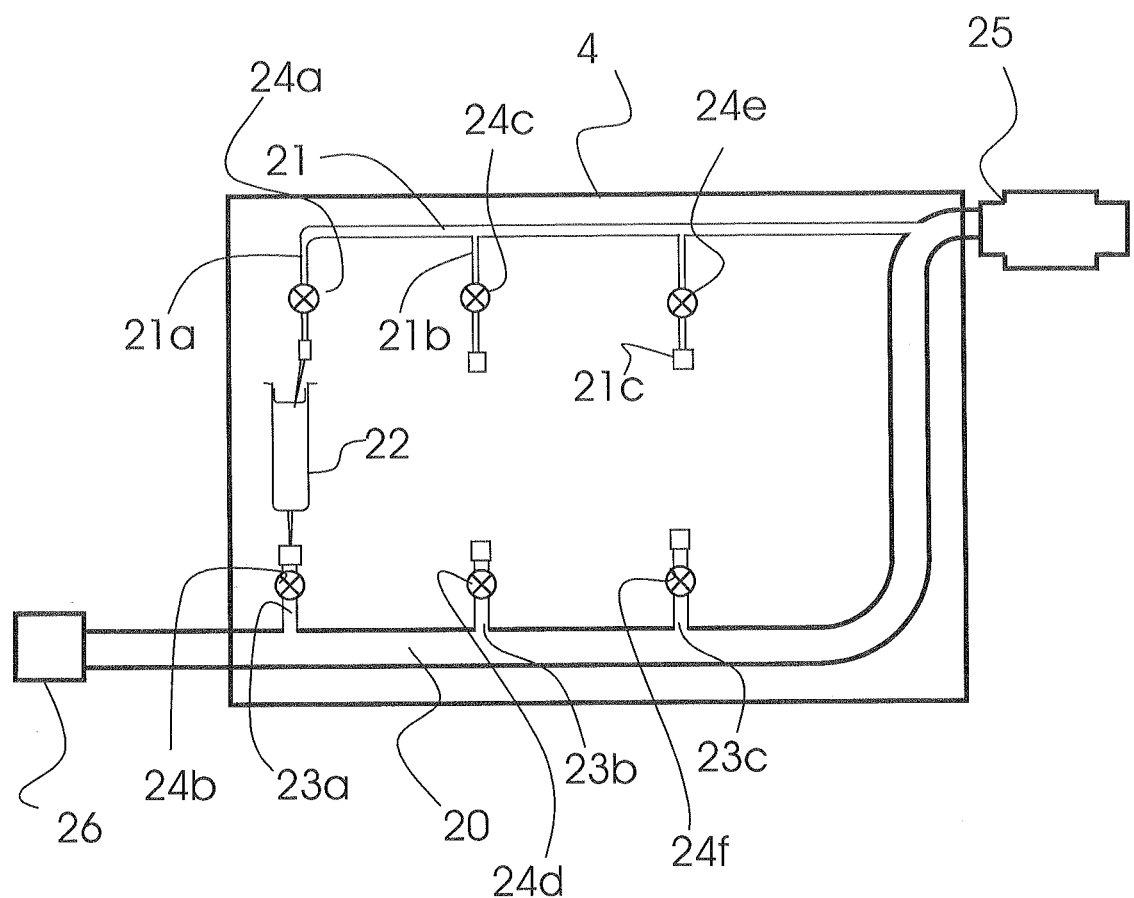
FIG. 2 is a cross section of a manifold for a dialysis machine.

FIG. 2 shows an enlarged cross section of the manifold 4. The manifold 4 comprises a main line 20, a first section 21 and a second section of a bypass line. The first section 21 of the bypass line comprises two or more branch-offs 21b and 21c each of which is connectable with an inlet of a pharmaceutical container like a syringe 22 or a vial. For this reason, the shown end 21a of the first section comprises a needle penetrating the piston of the shown syringe 22. Thus, the end 21a of the first section 21 is also connectable with a pharmaceutical container. The needle or luer cone of the syringe 22 is connected with a second section 23a of the bypass line. The second section 23a of the bypass line leads to the main line 20. There are two further second sections 23b and 23c corresponding with the branch-off 21b and the end 21c of the first section 21 each of which are connectable with an outlet of a pharmaceutical container. As a rule, the cross sections of the bypass line are smaller than the cross section of the main line 20. The bypass line comprises six membrane valves 24a, 24b, 24c, 24d, 24e and 24f for controlling the flow through pharmaceutical containers 22 inserted into the manifold. The inlet connector 25 of the mainline 20 corresponds with the outlet connector of the dialyzer 6 and is a dialyzer connector 25. The outlet connector 26 of the main line 20 corresponds with the outlet connector of a dialyzer as also shown in FIG. 1. During a dialysis session, blood is flowing from the inlet 25 through the main line 20 to the outlet 26. If for example the valves 24a and 24b are open, a part of the blood flowing through the manifold 4 flows through the bypass line and thus through the shown syringe 22. As a result, the pharmaceutical content of the syringe flows into the main line.

If the outlet of the manifold is connected with an inlet of the dialyzer, the outlet of the manifold comprises the dialyzer connector 25 to connect the manifold outlet to the dialyzer.

Figure 3A:
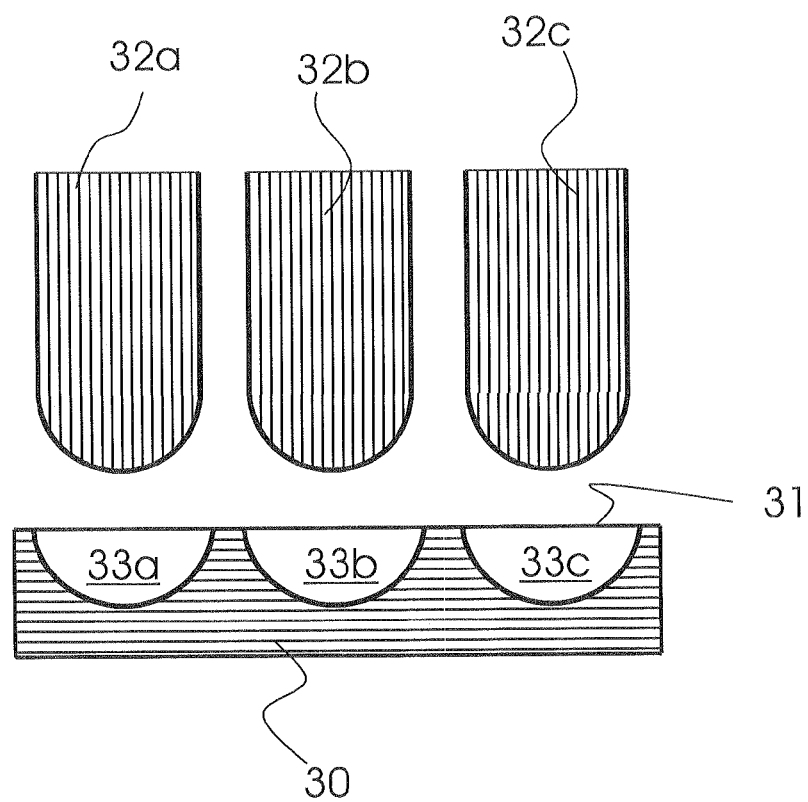
FIGS. 3a and 3b are cross sections of membrane valves.
Figure 3B:
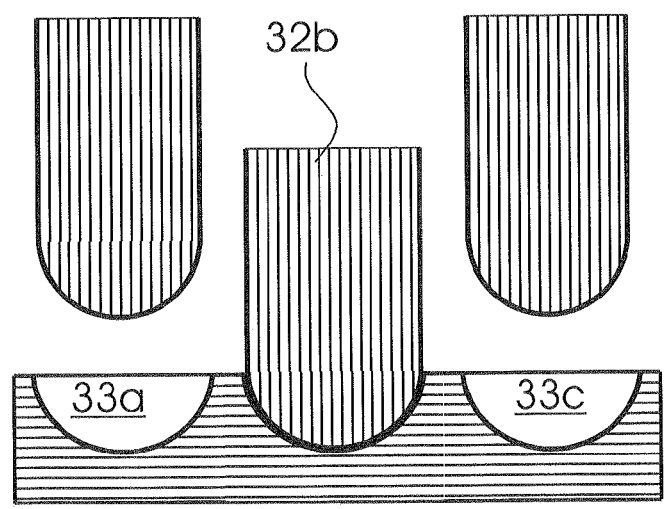

FIG. 3a shows a cross section of three membrane valves composed of one housing 30, one membrane 31 and three moveable bolts 32a, 32b and 32c. The housing 30 comprises a first flow path 33a of the first valve, a second flow path 33b of the second valve and a third flow path 33c of the third valve. The membrane 31 covers all flow paths 33a, 33b and 33c and is deflectable towards each flow path by the bolts 32a, 32b and 32c. The design shown in FIG. 3a saves space. The production costs are low. FIG. 3b refers to the situation that the second valve is closed for example by a pre-stressed spring (not shown) or magnetic means (not shown).

Figure 3C:
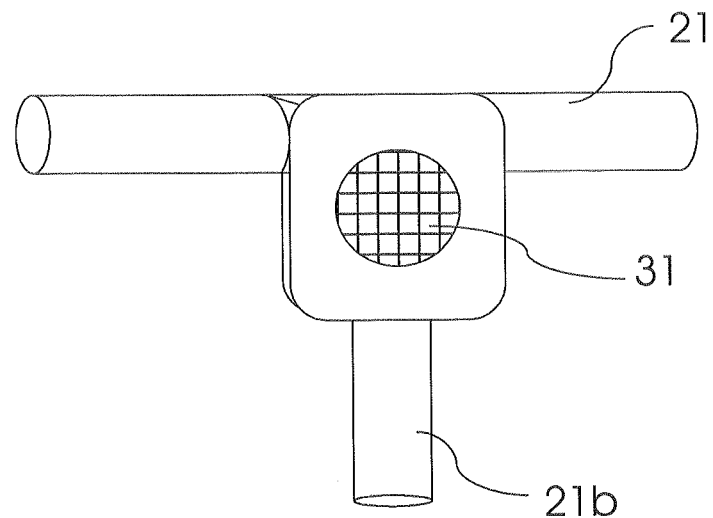
FIG. 3c is a perspective view of a membrane valve.

FIG. 3c is a perspective view of an embodiment of the membrane valve. The housing of the membrane valve may be made in one piece with a tube and a branch-off as shown in FIG. 3c. For example, the tube may be the section 21 of a bypass-line connected with the branch-off 21b according to FIG. 2. If a pressure is applied to the membrane 31, the path through the section 21b is closed. FIG. 3c shows that a very space-saving construction is possible. Instead of only one membrane valve, it is possible to provide a lot of membrane valves each valve comprising a branch-off according to FIGS. 3a and 3b.

Figure 4A:
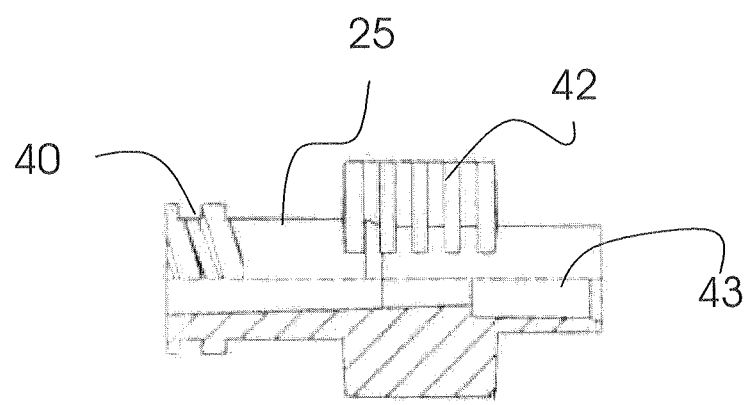
FIG. 4a is a dialyzer connector.
Figure 4B:
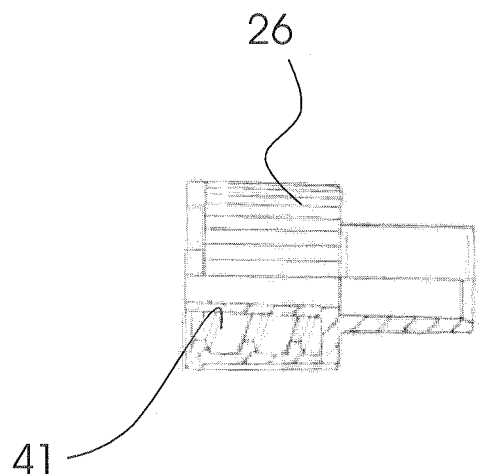
FIG. 4b is a female connector for a dialyzer connector.

FIG. 4a shows the dialyzer connector 25 and FIG. 4b the corresponding female connector 26 of a dialyzer. One end of the dialyzer connector 25 comprises a male thread 40 and an end of the female connector a corresponding female thread 41. The dialyzer connector comprises a grip 42 in order to facilitate the handling of the dialyzer connector. The other end 43 of the dialyzer connector is adapted to a tube of a dialysis machine. The other end of the female connector 26 may also be adapted to a tube of a dialysis machine so that it is possible to fix a tube end at the connector.

Figure 5:
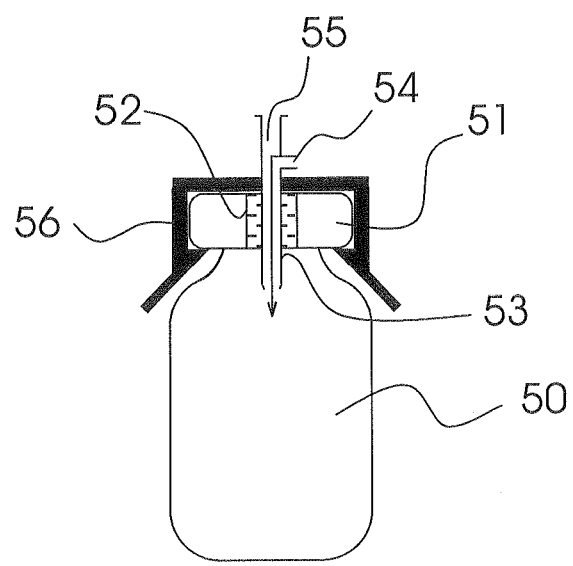
FIG. 5 is a vial with an adapter.

FIG. 5 shows an ampoule respectively a vial 50 with a lid 51. The lid 51 comprises a pierceable rubber stopper 52. An adapter for the vial comprises a hollow needle 53 with an inlet (venting) path 54 and an outlet path 55 (vial adapter, vented). The needle 53 penetrates the rubber stopper 52. Additionally, the adapter comprises a clamp 56 in order to fix the adapter at the lid 51.

According to the state of the art, an adapter for a vial as shown in FIG. 5 comprises a female luer lock. In an embodiment of the invention, the outlet of the adapter comprises a male luer lock in order to facilitate the connection between the outlet of the adapter with an injection site of a dialysis machine since the injection site of a dialysis machine usually comprises a female luer lock.

The vial 50 of FIG. 5 may be inserted in a manifold according to FIG. 2 or 1. If is then necessary to connect the first section of the bypass line with the inlet path of the adapter and the second section with the outlet path of the adapter.

Figure 6:
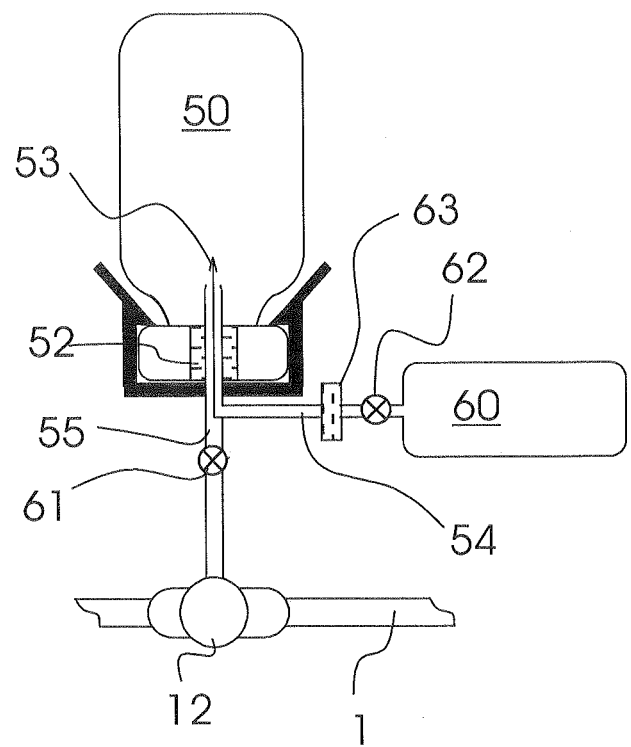
FIG. 6 is the vial and the adapter of FIG. 5 connected to an injection site of a dialysis machine.

FIG. 6 shows the vial 50 and the adapter of FIG. 5. The outlet path 55 of the adapter is connected with an injection site 12 of the tube 1 and thus to a tube on the inlet side of the pump. The inlet path 54 of the adapter is connected with a gas container 60 which is either collapsable or rigid.

In order to start the administration, it is necessary to open the valve 61. Due to the suction force generated by the pump, the pharmaceutical flows through the outlet path 55 into the tube 1. As a result, gas flows from the gas container 60 through the inlet path 54 into the pharmaceutical container 50. This generates a low pressure within the gas container 60. As soon as the low pressure force corresponds with the suction force, the flow of the pharmaceutical stops. The period from the beginning to the end of the administration depends on the cross sections of the inlet path, the outlet path and the volume of the gas container 60.

The connection between the gas container and the pharmaceutical container may comprise a pressure reducer 62 in order to adjust the flow rate of the pharmaceutical. Additionally, the connection between the gas container and the pharmaceutical container may comprise a disposable microbe pertaining filter 63 in order to avoid a contamination of the pharmaceutical.

If the outlet path 55 is connected with an injection site 12 of the tubes 1b or 5, the gas in the gas container 60 is under pressure. The gas container may be a balloon which would save costs.

Figure 7:
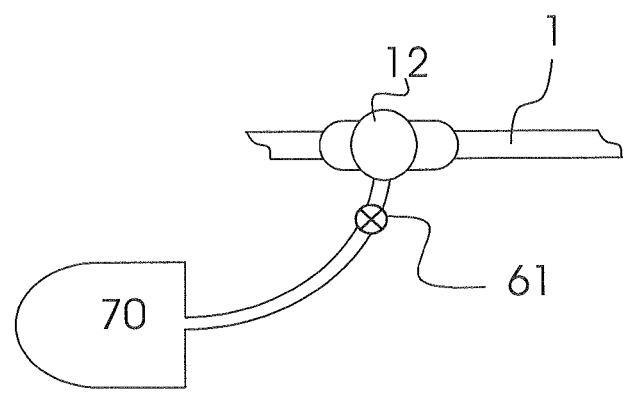
FIG. 7 is a collapsible pharmaceutical container connected with an injection site.

In the embodiment of FIG. 7, a collapsible pharmaceutical container 70 is connected with an injection site 12 of the first tube 1. The administration of the pharmaceutical stops as soon as the flexible container 70 is empty.

Instead of connecting the outlet of a pharmaceutical container shown in FIG. 5, 6 or 7 with an injection site, the outlet may be connected with a main line of a manifold. It is then necessary to replace a section of a tube by the main line of the manifold. Preferably, the manifold can contain at least two pharmaceutical containers connected with the main line. The manifold can comprise one or more gas containers connectable with pharmaceutical containers. If the pharmaceutical container is a syringe, the gas container may comprise a needle for the connection. If the pharmaceutical container is a vial, the gas container may comprise a corresponding adapter for the connection.

In an embodiment, a manifold comprises different adapters respectively connecting means for inserting different pharmaceutical containers into the manifold. In other words, it is then possible to connect a first pharmaceutical container containing for example Venofer® with an appropriate first adapter or connector but not with a further adapter or connector of the manifold. A second pharmaceutical container containing for example EPO may be connected with a second adapter or connector but not with a further adapter or connector of the manifold. A third pharmaceutical container containing for example the active form of vitamin D may be connected with a third adapter or connector but not with a further adapter or connector of the manifold. This embodiment of the invention helps to avoid mistakes due to human failure. It is for example not possible to connect a pharmaceutical container with a gas container having a wrong volume.

In an embodiment of the invention, the manifold comprises a first adapter for a syringe and a second adapter for a vial for the above mentioned reasons. In this case, the syringe always contains a first pharmaceutical, for example an iron preparation and the vial a second pharmaceutical for example EPO. In this way, it is not possible to insert a pharmaceutical container containing the first or the second pharmaceutical twice or in a wrong way.

The invention claimed is:

1. Dialysis machine comprising tubes (1, 5, 8) connected with a dialyzer (6), an apparatus (4) for delivering pharmaceuticals into the tubes (1, 5, 8), and a pump (11) for the transport of blood through the tubes (1, 5, 8) and the dialyzer (6), wherein
the apparatus (4) is configured to administer at least one pharmaceutical by a pressure effect of the pump (11) and comprises
a main line (20) on an outlet side of the pump (11) and configured to be coupled to a first connector (25) at an inlet end thereof and a second connector (26) at an outlet end thereof,
a first section of a bypass line (21, 21a, 21b, 21c) branching off the mainline (20) downstream of the inlet end of the main line (20) and configured for connecting the main line (20) with a container (22) containing a pharmaceutical at an outlet end of the first bypass section (21a, 21b, 21c), and
a second section (23a, 23b, 23c) of the bypass line branching off the main line (20) directly downstream of the first bypass section (21, 21a, 21b, 21c) and upstream of the outlet end of the main line (20), and configured for connecting the container (22) containing a pharmaceutical at an inlet end of the second bypass section (23a, 23b, 23c) with the main line (20).

2. Dialysis machine according to claim 1, comprising a small cross section of an inlet path into one of tubes for the at least one pharmaceutical so that at least five minutes, preferably at least ten minutes are necessary to administer the total volume of the at least one pharmaceutical.

3. Dialysis machine according to claim 1, wherein the at least one pharmaceutical is EPO, an iron preparation and/or the active form of vitamin D.

4. Dialysis machine according to claim 1, all containers (22, 50) containing pharmaceuticals for carrying out a dialysis are connected with the dialysis machine at the same time.

5. Dialysis machine according to claim 1, a control device for controlling the activation of the delivery of the at least one pharmaceutical.

6. Dialysis machine according to claim 1, comprising at least one membrane valve (30, 31, 32a, 33a) to control the delivery of a pharmaceutical.

7. Dialysis machine according to claim 6, comprising at least two membrane valves and only one membrane (31) stretching across the housing (30) or housings of the at least two membrane valves.

8. Dialysis machine according to claim 1, comprising a membrane valve to control the delivery of a pharmaceutical, wherein the membrane valve comprises a housing (30), a membrane (31), a movable bolt (32a, 32b, 32c) and an electric, pneumatic, hydraulic or magnetic device for the movement of the bolt (32a, 32b, 32c).

9. Dialysis machine according to claim 1, comprising
a collapsible container (70) free of gas connected with a tube (1) on an inlet side (1a) of the pump (11), wherein the container (70) contains a pharmaceutical, or
a non-flexible and non-collapsible container (50) connected with a tube (1) on the inlet side (1a) of the pump, wherein the container (50) contains a pharmaceutical and a gas.

10. Dialysis machine according to claim 9, wherein the non-flexible and non-collapsible container is a syringe or a vial (50) with a pierceable rubber stopper (52).

11. Dialysis machine according to claim 10, comprising a connection between the piston of the syringe and a container (60) containing a gas.

12. Dialysis machine according to claim 1, wherein cross sections which determine the flow rate of the pharmaceutical during the administration are so designed such that the administration lasts for at least five minutes, preferably for at least ten minutes.

13. Dialysis machine according to claim 1, wherein the cross sections which determine the flow rate of the pharmaceutical during the administration are designed such that the administration lasts for up to thirty minutes, preferably for up to twenty minutes.

14. Dialysis machine according to claim 1, wherein the apparatus for administering the at least one pharmaceutical comprises a manifold (4) comprising the mainline (20) and the bypass line (21, 21a, 21b, 21c, 23a, 23b, 23c) for providing the flow from the main line (20) through the pharmaceutical container (22) connectable with the bypass line (21, 21a, 21b, 21c, 23a, 23b, 23c), wherein the main line (20) is detachably connected with the dialyzer (6) at one end and with a tube (1, 5) at the other end.

15. Method for a dialysis comprising the step of administration of a pharmaceutical by a dialysis machine according to claim 1 by a pressure effect of the pump.

16. Method according to claim 15, wherein the administration of the pharmaceutical lasts at least five minutes, preferably at least ten minutes.

17. Method according to claim 15, wherein the pharmaceutical is an iron preparation.

18. Dialysis machine according to claim 1, wherein no other connections or dialysis elements are directly positioned in the main line (20) between branching off of the first (21, 21a, 21b, 21c) and second (23a, 23b, 23c) sections of the bypass line.

* * * * *